(12) United States Patent
Collard et al.

(10) Patent No.: US 11,579,068 B2
(45) Date of Patent: Feb. 14, 2023

(54) MEASURING SYSTEM AND MANUFACTURING PROCESS OF SUCH A MEASURING SYSTEM

(71) Applicants: Centre National de la Recherche Scientifique (CNRS), Paris (FR); Neuroindx, Inc., Torrance, CA (US); The Foundation for the Promotion of Industrial Science, Tokyo (JP)

(72) Inventors: Dominique Collard, Lambersart (FR); Hiroyuki Fujita, Tokyo (JP); Stanislav Karsten, Rancho Palos Verdes, CA (US)

(73) Assignees: Centre National de la Recherche Scientifique (CNRS), Paris (FR); Neuroindx, Inc., Torrance, CA (US); The Foundation for the Promotion of Industrial Science, Tokyo (JP)

( * ) Notice: Subject to any disclaimer, the term of this patent is extended or adjusted under 35 U.S.C. 154(b) by 862 days.

(21) Appl. No.: 16/468,357

(22) PCT Filed: Dec. 12, 2017

(86) PCT No.: PCT/EP2017/082374
§ 371 (c)(1),
(2) Date: Jun. 11, 2019

(87) PCT Pub. No.: WO2018/108880
PCT Pub. Date: Jun. 21, 2018

(65) Prior Publication Data
US 2019/0310178 A1 Oct. 10, 2019

(30) Foreign Application Priority Data
Dec. 12, 2016 (EP) .................................... 16306668

(51) Int. Cl.
*G01N 15/10* (2006.01)
*B01L 3/00* (2006.01)
(Continued)

(52) U.S. Cl.
CPC .... *G01N 15/1056* (2013.01); *B01L 3/502761* (2013.01); *G01N 3/08* (2013.01);
(Continued)

(58) Field of Classification Search
None
See application file for complete search history.

(56) References Cited

U.S. PATENT DOCUMENTS

2014/0128285 A1   5/2014   Rowat et al.

FOREIGN PATENT DOCUMENTS

DE   202014003175 U1   4/2015
JP   2016099219 A   5/2016

OTHER PUBLICATIONS

Kumemura et al., "Direct bio-mechanical sensing of enzymatic reaction On DNA by silicon nanotweezers," 2010 IEEE 23rd International Conference on Micro Electro Mechanical Systems (MEMS), 2010, pp. 915-918, doi: 10.1109/MEMSYS.2010.5442356. (Year: 2010).*

(Continued)

*Primary Examiner* — Rebecca M Giere
(74) *Attorney, Agent, or Firm* — Banner & Witcoff, Ltd.

(57) ABSTRACT

The invention relates to a system (10) adapted to measure multiple biophysical characteristics of cells, the system (10) comprising: a microfluidic chip (12) provided with a microfluidic channel (14) which allows cells to flow through, the microfluidic channel (14) having an inlet (14a), an outlet (14b), and a lateral opening (14c) situated between the inlet (14a) and the outlet (14b); and a capacitive sensor (30) integrated in the microfluidic chip, adapted to obtain bio- (Continued)

physical characteristics of a single cell in the microfluidic channel (14) by directly manipulating the single cell by sensor elements (31, 32) through the lateral opening (14c) of the microfluidic channel (14), the sensor (30) comprising a stationary part and an electrostatically driven movable part which is movable relative to the stationary part, the stationary part being fixed to the microfluidic chip (12), the movable part being arranged in the lateral opening (14c) of the microfluidic channel (14), wherein a portion of the sensor elements (31, 32) provides an interface between fluid and air in the system.

17 Claims, 17 Drawing Sheets

(51) Int. Cl.
G01N 3/08 (2006.01)
G01N 33/487 (2006.01)
G01N 3/32 (2006.01)
G01N 1/10 (2006.01)

(52) U.S. Cl.
CPC ........... *G01N 3/32* (2013.01); *G01N 15/1031* (2013.01); *G01N 33/48728* (2013.01); *B01L 2200/0652* (2013.01); *B01L 2300/0627* (2013.01); *B01L 2300/0663* (2013.01); *B01L 2300/0816* (2013.01); *B01L 2300/0867* (2013.01); *B01L 2400/049* (2013.01); *G01N 2001/1056* (2013.01); *G01N 2015/105* (2013.01); *G01N 2015/1006* (2013.01); *G01N 2015/1081* (2013.01); *G01N 2015/1093* (2013.01); *G01N 2203/0089* (2013.01); *G01N 2203/0286* (2013.01)

(56) References Cited

OTHER PUBLICATIONS

Nakahara, Kou et al. "On-Chip Transportation and Measurement of Mechanical Characteristics of Oocytes in an Open Environment", Micromachines, vol. 6, No. 5, May 22, 2015. pages 648-659, XP055378372.

Lafitte et al.—"Integrated MEMS platform with silicon nanotweezers and open microfluidic device for real-time and routine biomechanical probing on molecules 25 and cells,"—35th Annual International Conference of the IEEE EMBS, Osaka, Japan, Jul. 3-7, 2013, pp. 148-151.

Kudo et al.—"Novel Cell and Tissue Acquisition System (CTAS): microdissection of live and frozen brain tissues"—PLoS One. 2012;7(7):e41564. doi:10.1371/journal.pone.0041564. Epub Jul. 24, 2012. PMID: 22855692.

Yamahata et al.—"Silicon Nanotweezers With Subnanometer Resolution for the Micromanipulation of Biomolecules,"—J. Microelectromech Syst., vol. 17, No. 3, pp. 623-631, 2008.

* cited by examiner

MEASURING SYSTEM AND MANUFACTURING PROCESS OF SUCH A MEASURING SYSTEM

RELATED APPLICATION DATA

The present application is a National Stage Application under 35 U.S.C. 371 of PCT application number PCT/EP2017/082374 designating the United States and filed Dec. 12, 2017; which claims the benefit of EP application number 16306668.1 and filed Dec. 12, 2016, each of which are hereby incorporated herein by reference in their entireties.

FIELD OF THE INVENTION

The present invention relates to a measuring system used for biophysical characterization of cells and to a manufacturing process of such a measuring system.

BACKGROUND OF THE INVENTION

In the field of biomedical sciences, there has been a great demand for solutions to determine biophysical characteristics of individual cells. The biophysical characteristics of cells provide useful information to identify a relationship between the cell and a certain disease, such as cancer.

On the other hand, a mixture of cells having different biophysical characteristics only produces the averaged results, making it difficult to identify disease specific changes found only in specific subanatomical regions or cell types.

Japanese Patent Publication No. 2016-099219 discloses a detection system for detecting a reaction of a molecule within a microfluidic channel under the influence of a certain reactant. According to this system, the reaction of a molecule can be observed through direct manipulations of the molecule by using a pair of tweezers.

Tweezers designed to capture a single cell between their flat tips have also been known. See Nicolas Lafitte, Hervé Guillou, Momoko Kumemura, Laurent Jalabert, Teruo Fujii, Hiroyuki Fujita, and Dominique Collard, "Integrated MEMS platform with silicon nanotweezers and open microfluidic device for real-time and routine biomechanical probing on molecules and cells," 35th Annual International Conference of the IEEE EMBS, Osaka, Japan, 3-7 Jul. 2013, pp. 148-151.

These tweezers are introduced into the microfluidic channel through an opening formed in a side wall of the microfluidic channel to capture and directly manipulate a cell or molecule between the tweezers. In order to do so, however, the existing tweezers require accurate positioning relative to the microfluidic channel. This positioning process can be very difficult and considered to be a burden when it is desired to increase the throughput of the system (the number of objects which can be characterized by the system during a certain period of time).

Therefore, an object of the present invention is to provide a measuring system which provides efficient characterizations of individual cells and makes it possible to easily increase the throughput of the system.

SUMMARY OF THE INVENTION

According to an embodiment of the invention, there is provided a system adapted to measure multiple biophysical characteristics of cells, the system comprising:

a microfluidic chip provided with a microfluidic channel which allows cells to flow through, the microfluidic channel having an inlet, an outlet, and a lateral opening situated between the inlet and the outlet; and a capacitive sensor integrated in the microfluidic chip, adapted to obtain biophysical characteristics of a single cell in the microfluidic channel by directly manipulating the single cell by sensor elements through the lateral opening of the microfluidic channel, the sensor comprising a stationary part and an electrostatically driven movable part which is movable relative to the stationary part, the stationary part being fixed to the microfluidic chip, the movable part being arranged in the lateral opening of the microfluidic channel, wherein a portion of the sensor elements provides an interface between fluid and air in the system.

According to an embodiment, the sensor elements may include a pair of arms extending toward each other, tips of the pair of arms are arranged in the lateral openings formed on opposite side of the microfluidic channel, and at least one arm of the pair of arms is capable of moving closer to or away from the other arm.

According to an embodiment, the lateral openings have a size selected to allow the tips of the arms to be introduced into the microfluidic channel through the respective opening while preventing a fluid within the microfluidic channel from leaking.

According to an embodiment, the sensor may be a programmable sensor adapted to selectively obtain one or more biophysical characteristics of the single cell.

According to an embodiment, the microfluidic chip may be further provided with at least one additional microfluidic channel arranged in parallel with the microfluidic channel.

According to an embodiment, the sensor may be adapted to obtain biophysical characteristics of the single cell by stimulating the single cell in the microfluidic channel mechanically and/or electrically.

According to an embodiment, the sensor may be adapted to obtain biophysical characteristics of the single cell by stimulating the single cell in the microfluidic channel chemically and/or biologically.

According to an embodiment, the sensor may be adapted to obtain biophysical characteristics including at least one of size, rigidity, shape recovery time, viscosity, and electrical impedance, and/or frequency dependency of the biophysical characteristics.

According to an embodiment, the measuring system may further comprise a collecting means in fluid communication with the outlet of the microfluidic channel.

According to an embodiment, the measuring system may further comprise a sorting means for sorting the cells flowing in the microfluidic channel, depending on the biophysical characteristics of the cells obtained by the sensor.

According to an embodiment, the microfluidic chip may be further provided with at least one branch channel branching off from the microfluidic channel and downstream relative to the sensor.

According to an embodiment, the sorting means may comprise a valve adapted to direct the cell to the branch channel or downstream of the microfluidic channel, depending on the biophysical characteristics of the cell.

According to an embodiment, the measuring system may further comprise a dock in fluid communication with the branch channel.

According to an embodiment, the sorting means may be adapted to sort the cells by comparing the biophysical characteristics of the cell with a threshold.

According to an embodiment, the threshold may be programmable.

According to an embodiment, there is provided a process of manufacturing the measuring system. The process comprising: applying a mask pattern corresponding to the shape of the microfluidic channel and the shape of the stationary part and the movable part of the sensor; and forming the shape of the sensor together with the microfluidic channel.

Another object of the invention relates to a process of measuring multiple biophysical characteristics of cells, comprising:
providing a system as described above;
flowing cells through the microfluidic channel between the inlet and the outlet;
directly manipulating a single cell by the sensor through the lateral opening of the microfluidic channel so as to obtain biophysical characteristics of said single cell.

According to an embodiment, the process further comprises stimulating the cell chemically and/or biologically in the microfluidic channel.

According to an embodiment, the process further comprises sorting the cells flowing in the microfluidic channel depending on the biophysical characteristics of the cells obtained by the sensor.

The biophysical characteristics of the cell may include at least one of size, rigidity, shape recovery time, viscosity, and electrical impedance, and/or frequency dependency of the biophysical characteristics.

BRIEF DESCRIPTION OF THE FIGURES

Embodiments of the invention will be described in further detail with reference to the accompanying drawings, in which.

DETAILED DESCRIPTION OF EMBODIMENTS OF THE INVENTION

Figure 1:
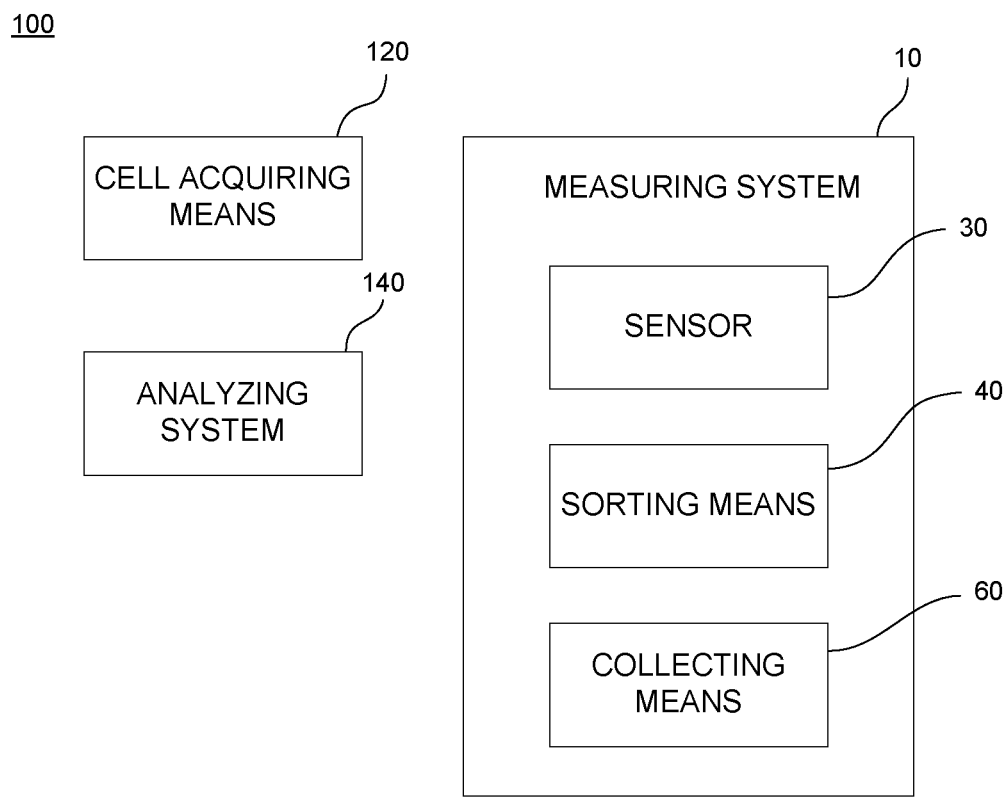
FIG. 1 is a schematic diagram showing an exemplary configuration of a cell analysis system which includes a measuring system according to an embodiment.

FIG. 1 shows a cell analysis system 100 which includes a measuring system 10 according to an embodiment of the present invention. The cell analysis system 100 also includes a cell acquiring means 120 and an analyzing system 140.

The cell acquiring means 120 has functions of acquiring cells individually from cell mixtures. The cell mixtures may be complex heterogeneous cells mixtures and tissues, which include but are not limited to any complex multicellular mixture, such as complex cell cultures, cell spreads, tissue sections (e.g., brain tissues), liquid biopsies, dissociated cells from solid biopsies. The cell acquiring means 120 may also be used to acquire cells from homogeneous populations in order to analyze individual cells. In the latter case, the analysis system 100 may be used to understand variability of individual cells among genetically or morphologically similar or identical cells.

The cell acquisition means 120 may be configured to aspirate and collect a single cell from cell mixtures by generating vacuum, as described in the U.S. Pat. No. 8,797,644. For example, the cells of interest are positioned directly under the tip of a disposable capillary unit (DCU), and a precise vacuum impulse is applied to collect the desired individual cells into the DCU barrel (see Kudo L C, Vi N, Ma Z, Fields T, Avliyakulov N K, Haykinson M J, Bragin A, Karsten S L. Novel Cell and Tissue Acquisition System (CTAS): microdissection of live and frozen brain tissues. PLoS One. 2012; 7(7):e41564. doi: 10.1371/journal.pone.0041564. Epub 2012 Jul. 24. PMID: 22855692). The acquired sample may be transferred into a container for subsequent use in the measuring system 10, or directly introduced into the measuring system 10.

The cell acquisition means 120 may employ laser-capture microdissection (LCM) which uses a laser to separate and collect individual cells. The cell acquisition means 120 may also employ fluorescence assisted cell sorting (FACS) technique which uses a specific fluorescent label to identify individual cells. Fluorescence assisted cell sorting instruments are capable of separating a heterogeneous suspension of cells into purified fractions on the basis of fluorescence and light scattering properties. Briefly, the cells to be analyzed are placed in suspension and injected into the measuring system 10.

Alternatively, cells can be captured directly from a microscope slide or petri dish, or collected simply by pipetting. Other types of devices may be used to isolate and collect single cells.

The measuring system 10 includes a sensor 30 adapted to obtain one or more biophysical characteristics of cells acquired by the cell acquiring means 120. The measuring system 10 may also include a sorting means 40 and a collecting means 60.

The sorting means 40 is capable of sorting the individual cells, depending on their biophysical characteristics. The sorted cells are collected by the collecting means 60 to ensure that the sorted cells are not mixed with other cells.

The analyzing system 140 performs further analysis of the collected cells as required. For example, the cells are subjected to molecular analysis, including but not being limited to cDNA synthesis, microarray analysis, proteomics applications, Next Generation Sequencing (NGS), etc.

According to the embodiment, the measuring system 10 is configured as an integrated system including a microfluidic channel through which cells are supplied and a sensor which obtains biophysical characteristics of the cells within the microfluidic channel.

Figure 2:
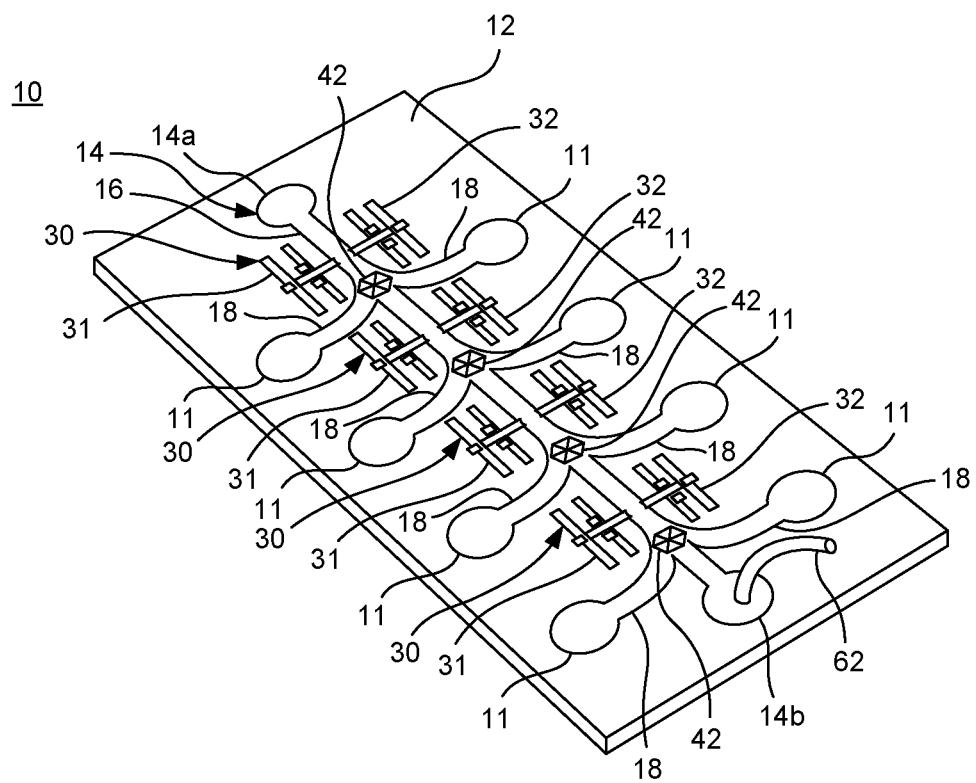
FIG. 2 is a schematic view showing a measuring system according to an embodiment.
Figure 3:
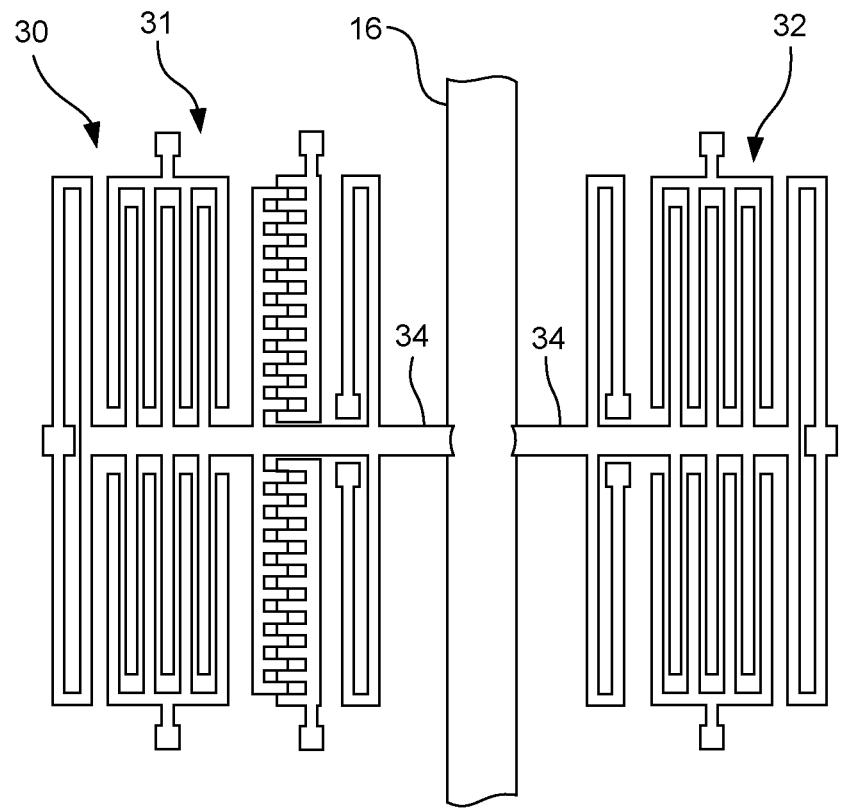
FIG. 3 is an enlarged view showing a sensor of the measuring system and part of a microfluidic channel nearby.
Figure 4:
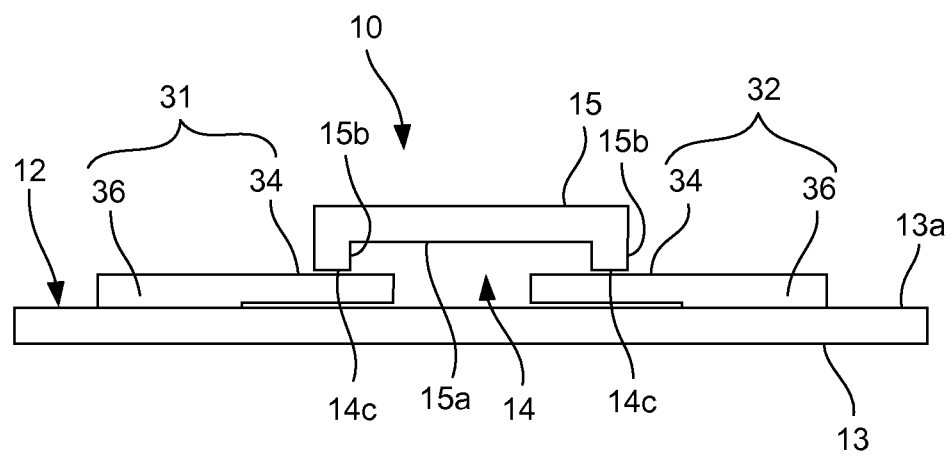
FIG. 4 is a cross sectional view schematically showing the measuring system.

Referring to FIGS. 2 to 4, the detailed configuration of an exemplary measuring system 10 will be described. FIG. 2 is a schematic view showing the measuring system 10. FIG. 3 is an enlarged view showing a sensor 30 of the measuring system 10 and part of a microfluidic channel 14 nearby. FIG. 4 is a cross sectional view schematically showing the measuring system 10.

The measuring system 10 includes a microfluidic chip 12 provided with a microfluidic channel 14. The microfluidic channel 14 has an inlet 14a at one end and an outlet 14b at the other end. The measuring system 10 also includes a plurality of sensors 30. In the illustrated embodiment, the measuring system 10 includes four sensors 30 arranged alongside the microfluidic channel 14.

As shown in FIG. 4, the microfluidic chip 12 includes a base plate 13 made of glass or silicon and a cover layer 15 disposed on an upper surface 13a of the base plate 13. The cover layer 15 may be made of polydimethylsiloxane (PDMS). The cover layer 15 has, on a surface facing the base plate 13, a groove 15a which is formed by a known way, e.g., by photolithography and structuration. The structuration may be performed by moulding. The microfluidic channel 14 is defined between the groove 15a and the side walls 15b of the cover layer 15 and the upper surface 13a of the base plate 13.

Returning to FIG. 2, the microfluidic channel 14 includes an elongated main channel 16 and branch channels 18. The main channel 16 extends between the inlet 14a and the outlet 14b. The branch channels 18 branch off from the main channel 16 and are disposed downstream of the respective sensors 30. In the illustrated embodiment, four pairs of branch channels 18 are formed in a spaced relationship with each other, and each pair of the branch channels 18 extends substantially laterally from both sides of the main channel 16 in opposite directions.

The microfluidic chip 12 is also formed with docks 11 which are provided at the terminal ends of the branch channels 18 and in fluid communication with the corresponding branch channels 18.

The microfluidic chip 12 also includes valves 42 as the sorting means 40 for sorting the cells based on their biophysical characteristics. The valves 42 are provided immediately downstream of the respective sensors 30. The valves 42 are configured to selectively guide cells either one of the branch channels 18 or downstream of the main channel 16. Accordingly, the cells having certain biophysical characteristics will be separated from the others by the valves 42.

The measuring system 10 also includes a suction unit 62. The suction unit 62 is arranged at the outlet 14b of the microfluidic channel 14. The suction unit 62 is operated by generating vacuum through a vacuum pump (not shown) to collect the cells which have reached the outlet 14b. Similar suction units may also be provided at the docks 11.

Each of the sensors 30 has a pair of sensor elements 31 and 32 which are provided on the opposite sides of the main channel 16 and face each other across the main channel 16. The sensor elements 31 and 32 have arms 34 extending laterally (substantially perpendicularly to the main channel 16) and toward the main channel 16. Referring to FIG. 4, the sensor elements 31 and 32 also have a base part 36 which is fixedly attached to the base plate 13 of the microfluidic chip 12.

The arms 34 project into the main channel 16 through openings 14c formed in the side walls 15b of the cover layer 15 which define the main channel 16. The openings 14c are small enough to prevent a fluid within the main channel 16 from leaking, but at the same time, large enough to allow the tip end of the arms 34 of the sensor 30 to be introduced into the main channel 16 through the opening 14c. The sensor elements 31 and 32 have the size in the order of micrometers or nanometers. In this way, the sensor elements (and more particularly the tip ends of the arms 34) provide an interface between fluid and air in the system. Thus, apart from the parts of the sensor elements that are in contact with the cell within the microfluidic channel, the sensor is within air, which avoids any damping of its components and thus provides for a greater accuracy of the measurement.

At least one of the sensor elements 31 and 32 includes a movable part which is movable together with the arm 34 relative to the remaining part (e.g., the base part 36). The movable part of the sensor element 31 or 32 may be electrostatically actuated by an actuator based on known Micro Electro Mechanical systems (MEMS). The movable part of the sensor elements 31 or 32 may also be thermally actuated or piezoelectrically actuated.

Thanks to the fluid-air interface that is provided by the sensor elements, the actuator remains within air, which avoids any damping of the electrostatic actuation.

Accordingly, the arms 34 of the sensor elements 31 and 32 are configured to move closer to or away from each other by the MEMS-based actuators. The tip ends of the arms 34 may be configured to facilitate capture of a single cell and/or sensing of the biophysical property of the cell captured between the arms 34. One of the sensor elements 31 and 32 may be configured as a passive sensor, which is fixed to the microfluidic chip 12. Thanks to the MEMS-based actuators, the sensor 30 is capable of stimulating single cells mechanically and/or electrically. The stimulation to the cells may be performed various ways. The cells may be subjected to the measurement of electrical properties under mechanical stress or of mechanical properties under electrical stimulation. In order to electrically stimulate the cells, the arms 34 may be able to act as electrodes.

The sensor 30 may be configured to measure more than one biophysical characteristics of the cells. The sensor 30 may be programmable to selectively obtain one or more biophysical characteristics of the cells.

The MEMS-based actuator may include a comb drive actuator, a parallel plate actuator, or a bimorph actuator. The MEMS-based actuators may be operated in accordance with a program to change a gap between the tips of the arms 34 in a controlled manner.

The displacement of the arms 34 may be detected as difference in capacitance. A known capacitive sensor can be used to detect a gap between the arms 34. A known piezo resistive sensor may also be used for the same purpose. The gap between the arms 34 may be detected in real-time.

The sensors 30 may also include a MEMS-based sensor element capable of detecting changes in mechanical or electrical properties of single cells in response to the actuation of the MEMS-based actuators. The MEMS-based sensor element and actuator may be incorporated into a single arm 34.

The sensor elements 31 and 32 are made from silicon substrate by using known technique such as reactive ion etching, local oxidation, and anisotropic etching in a similar manner as described in C. Yamahata, D. Collard, B. Legrand, T. Takekawa, M. Kumemura, G. Hashiguchi, and H. Fujita, "Silicon Nanotweezers With Subnanometer Resolution for the Micromanipulation of Biomolecules," J. Microelectromech. Syst., vol. 17, no. 3, pp. 623-631, 2008.

The manufacturing process of forming the sensor 30 according to an embodiment will be described below in further details.

The biophysical characteristics of the cells obtained by the sensor 30 include, but are not limited to, cell rigidity, size, shape recovery time, viscosity, and electrical impedance, or any combination thereof. The biophysical characteristics may be obtained as variables having a certain dependency on the resonance frequencies, the conductivities or dumping properties, etc.

The sensors 30 may also provide physical phenotyping of the cells. The cells may be categorized according to one or more mechanical, electrical and/or electromechanical properties.

Figure 5:
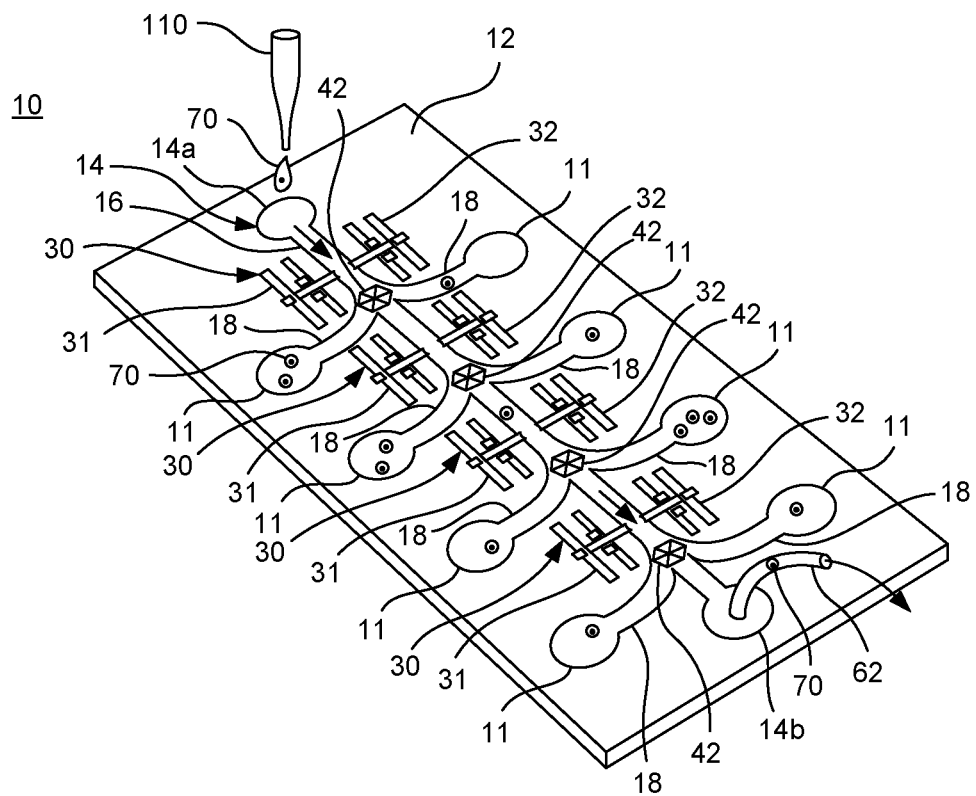
FIG. 5 is a schematic view corresponds to FIG. 2, but showing the measuring system in operation.

Now referring to FIGS. 5 and 6, the operation of the measuring system 10 will be described.

Cells 70 acquired by the acquiring means 120 are introduced to the inlet 14a of the microfluidic channel 14 by a known tool, such as a pipette 110. The cells 70 may be supplied to the microfluidic channel 14 consecutively at predetermined time intervals.

Figure 6:
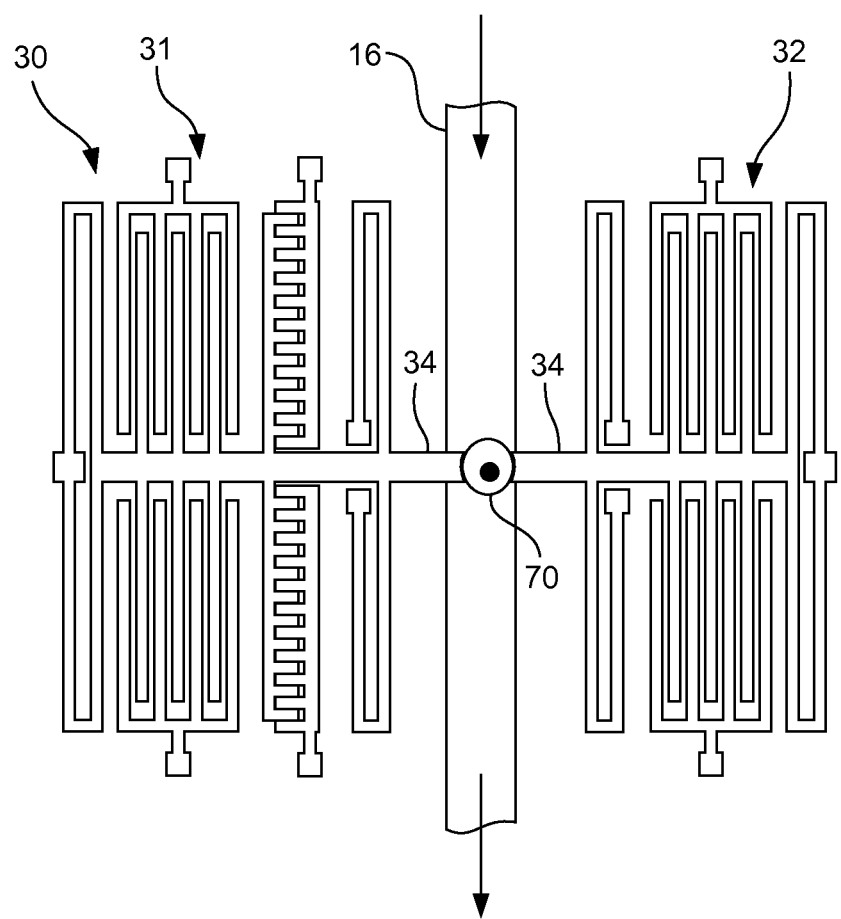
FIG. 6 is an enlarged view corresponding to FIG. 3, but showing the measuring system in operation.

When a cell 70 flowing in the main channel 16 reaches at one of the sensors 30, the sensor 30 is actuated to move the arm 34 of the sensor element 31 toward the other sensor element 32, for example, as illustrated in FIG. 6, to capture the cell 70 between the tips of the arms 34. The sensor 30 then manipulates the captured cell 70 electrically and/or mechanically for characterization of the cell with respect to its mechanical or electrical or electromechanical property or properties. According to an embodiment, it may take about one minute to measure the biophysical characteristics of the cell 70 by the sensor 30.

When the characterization is completed, the sensor 30 releases the cell 70, allowing it to proceed to the sorting stage. The valve 42 guides the cell 70 either downstream of the main channel 16 or to the branch channel 18, depending on the biophysical characteristics of the cell.

For example, if the rigidity of the cell 70 is within a certain range between a lower threshold and an upper threshold, the valve 42 directs the cell 70 downstream of the main channel 16 for further characterization. When the rigidity of the cell 70 is lower than the lower threshold, the cell 70 is directed to one of the branch channels 18 on the left side (the side of the sensor element 31). On the other hand, when the rigidity of the cell 70 is greater than the upper threshold, the cell 70 is directed to the other branch channel 18 on the opposite side (the side of the sensor element 32). Thresholds used for sorting cells 70 may be advantageously programmable.

The cell 70 flowing downstream of the main channel 16 is subjected to characterization by another sensor 30. The measuring system 10 according to the illustrated embodiment has four sensors 30, but may have any given number of sensors 30 as necessary. The measuring system 10 may include only one sensor 30 and one valve 42.

Each sensor 30 may obtain one or more biophysical characteristics of a cell, depending on the preferred application. Accordingly, the measuring system 10 with more than one sensor 30 can obtain different kinds of physical characteristics of the cells 70.

If a cell 70 flows through the main channel 16 to reach the outlet 14b, the cell 70 is sucked out of the microfluidic channel 14 by the suction unit 62 for further analysis by the analyzing system 140 as described above with reference to FIG. 1. In another embodiment, the cells 70 may be directly collected in a test tube which is connected to the outlet 14b of the microfluidic channel 14.

According to the above-described embodiment, the arm 34 of the sensor element 31 is actuated relative to the base part 36 which is fixedly attached to the microfluidic chip 12 and relative to the other arm 34 of the sensor element 32 on the opposite side. The integration of the sensor elements 31 and 32 with the microfluidic chip 12 eliminates a need to accurately position the sensor 30 relative to the microfluidic channel 14 every time the sensor 30 is introduced into the microfluidic channel 14. Therefore, the process of obtaining biophysical characteristics of the single cells 70 can be more efficient, compared to the existing technique.

In addition, since the sensor 30 is able to capture a cell 70 flowing within the microfluidic channel 14, cells 70 can be supplied to the microfluidic channel 14 one after another for consecutive characterization. This contributes to increasing the throughput of the measuring system 10.

Further, when the measuring system 10 includes a plurality of sensors 30 along the microfluidic channel 14, various biophysical characteristics of the cells 70 can be obtained during one continuous measuring process.

Furthermore, the cells 70 are sorted depending on their biophysical characteristics, while flowing through the microfluidic channel 14. As a result, only cells 70 having certain biophysical characteristics will reach the outlet 14b. Therefore, there is no need for additional means for separating cells subjected to a further analysis from others.

Figure 7A:
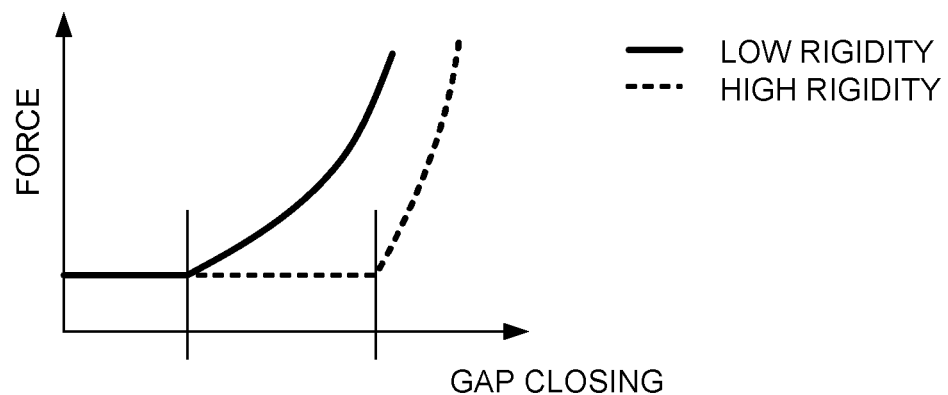
FIG. 7A to 7D show exemplary biophysical characteristics which can be obtained by the measuring system.
Figure 7B:
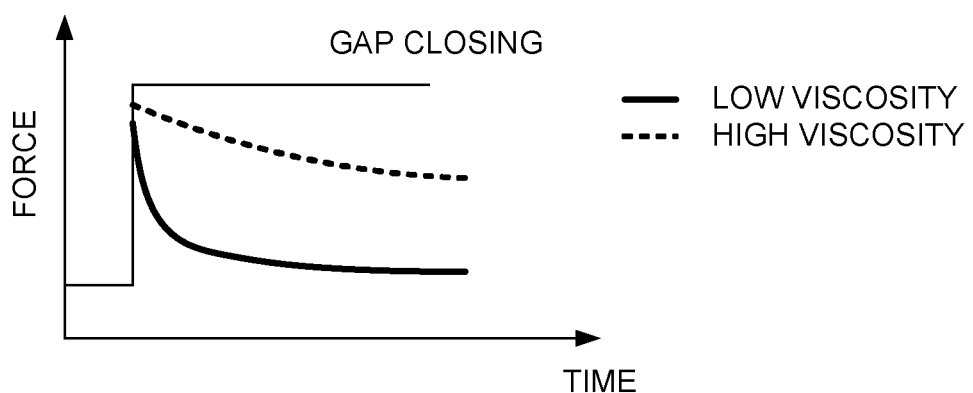

FIGS. 7A to 7D show examples of the biophysical parameters of cells obtained by the sensor 30. FIG. 7A shows force with respect to an amount of gap closing (a relative displacement between the arms 34 in a closing direction). A solid line in FIG. 7A represents one cell having lower rigidity and bigger cell size than another shown by a dashed line. FIG. 7B shows force with respect to time. A solid line in FIG. 7B represents one cell having low viscosity than another shown by a dashed line.

Figure 7C:
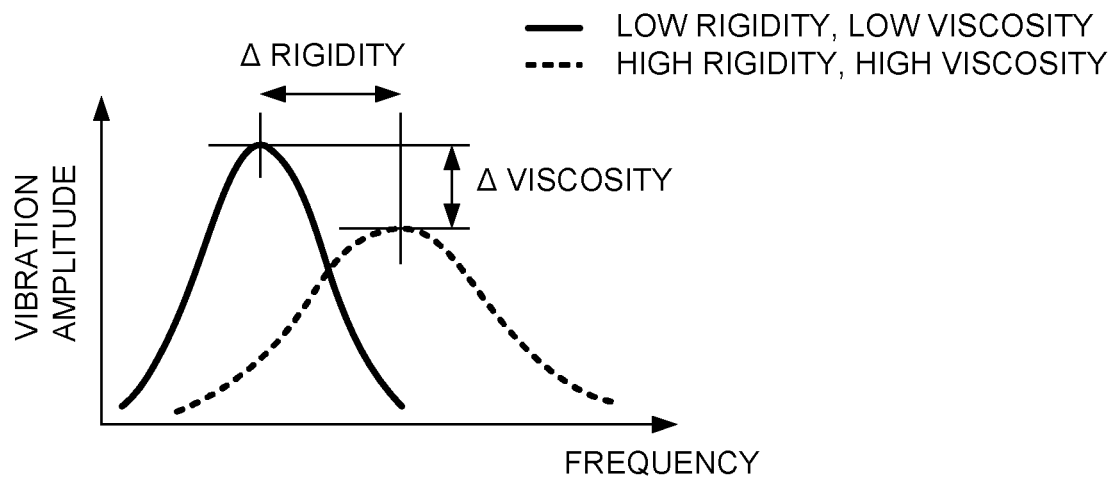

FIG. 7C shows the amplitude of vibration with respect to resonance frequency of the mechanical measurement. The resonance frequency is higher when the cell has higher rigidity. On the other hand, the peak of the vibration amplitude at the resonance frequency depends on the viscosity. The higher the viscosity of the cell, the smaller the peak at the resonance frequency becomes.

Figure 7D:
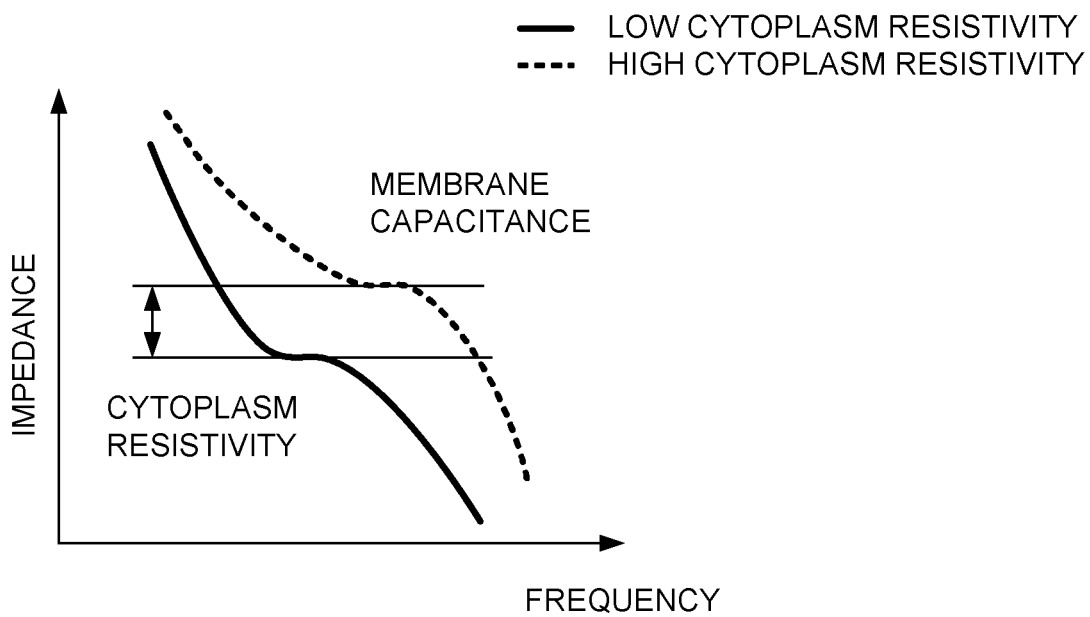

FIG. 7D shows electrical impedance with respect to resonance frequency of the electrical measurement. The solid line represents a cell having lower cytoplasm resistivity, which has lower impedance. The dashed line corresponds to a cell having a lower membrane capacitance, or in other words, higher impedance.

There is a well-established link between biophysical properties of the cells and a certain disease. For example, some recent studies have clearly demonstrated that cancer cells experience size modification and complex alterations of their mechanical properties.

Figure 8:
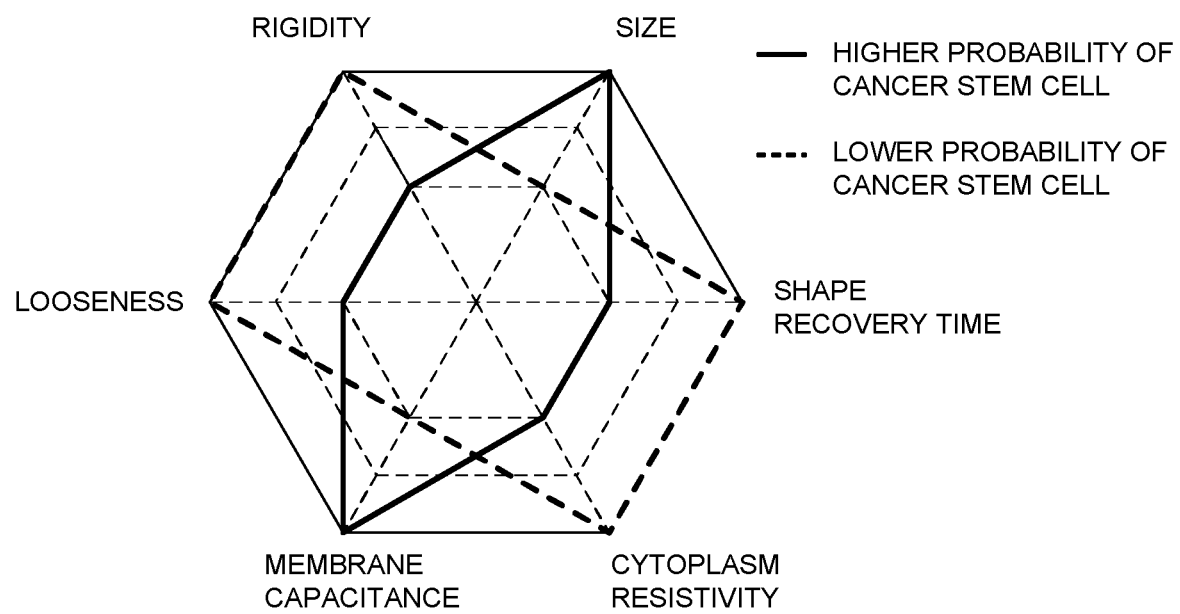
FIG. 8 shows an exemplary relationship between the biophysical characteristics of a cell and probability of being a cancer stem cell.

The biophysical characteristics of the cell provide a good indication of the link with a potential disease. FIG. 8 shows the difference in biophysical parameters between a cell having higher probability of being a cancer stem cell and a cell having lower probability. With such a known relationship between the biophysical characteristics of the cells and a potential disease, a person skilled in the art would easily determine appropriate threshold values for sorting the cells in terms of whether or not the cells are required for further analysis.

FIGS. 9A to 9E show various configurations of the sensor element. FIGS. 9A to 9E only show one sensor element 31, but the other sensor element 32 may also be configured in various ways. According to an embodiment, the sensor elements 31 and 32 can be configured as a modular device which can be combined with others. Therefore, the sensor 30 can have a modular design.

Figure 9A:
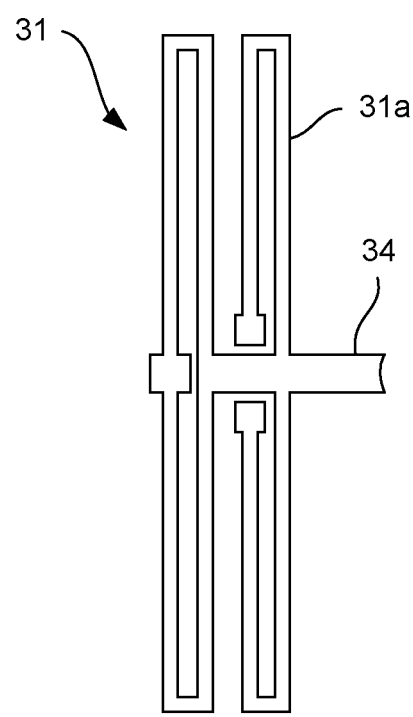
FIG. 9A to 9E show exemplary configurations of a sensor element of the measuring system.

For example, FIG. 9A shows a sensor element 31 including a flexible passive element 31a designed to come in contact with a cell for establishing electrical contact therebetween.

Figure 9B:
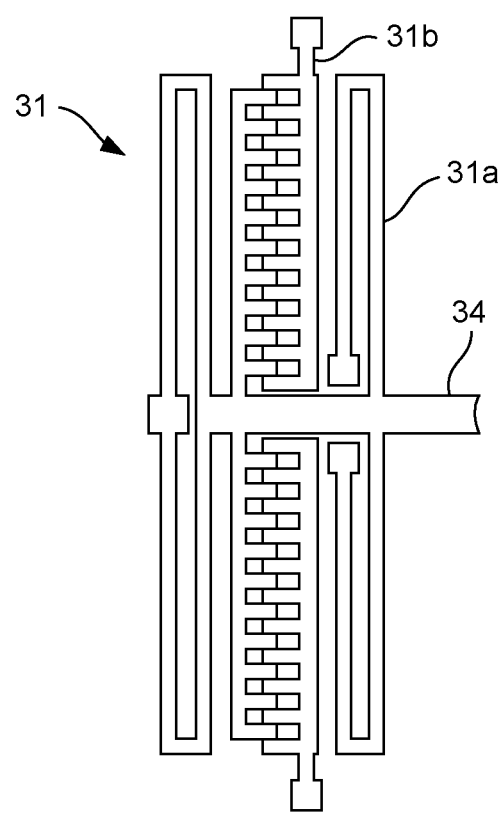

FIG. 9B shows a sensor element 31 including a combination of the passive element 31a as illustrated in FIG. 9A and an actuation element 31b. The actuation element 31b can be used to actuate the passive element 31a for mechanical or electrical stimulation of a cell.

Figure 9C:
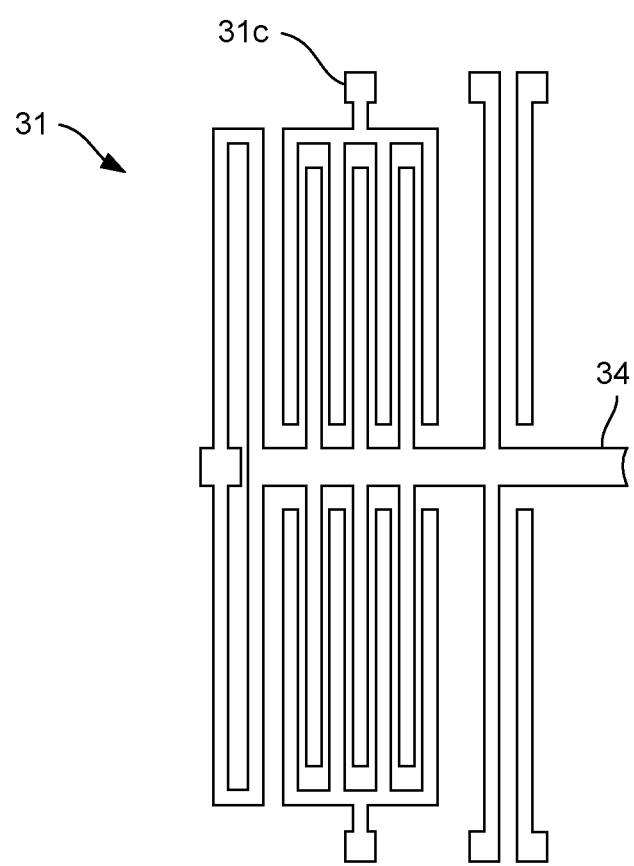

FIG. 9C shows a sensor element 31 including a harmonic sensing element 31c designed to provide for mechanical stimulation of a cell according to resonance frequency. The harmonic sensing element 31c can be used to obtain the biophysical characteristics of cells showing the dependency on the resonance frequency.

Figure 9D:
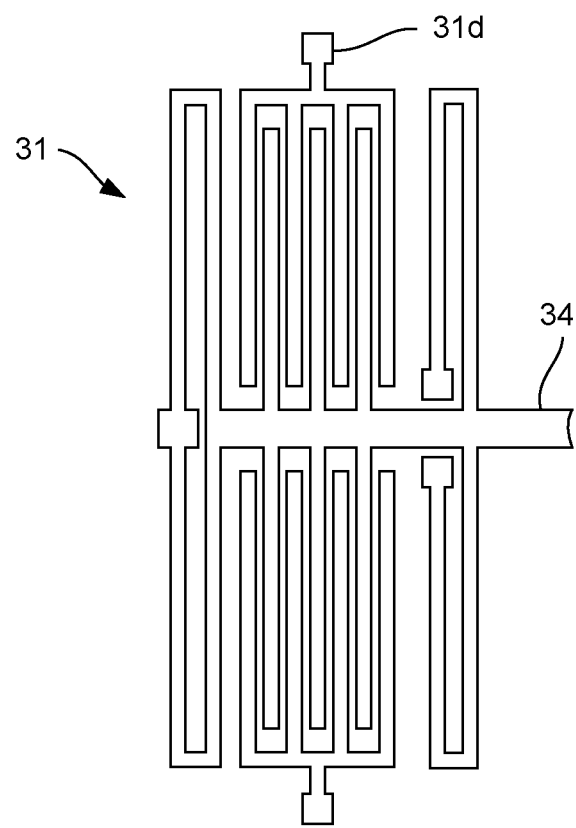

FIG. 9D shows a sensor element 31 including a displacement sensing element 31d. This type of the sensor element 31 does not have an actuating means and can be operated only in a passive manner.

Figure 9E:
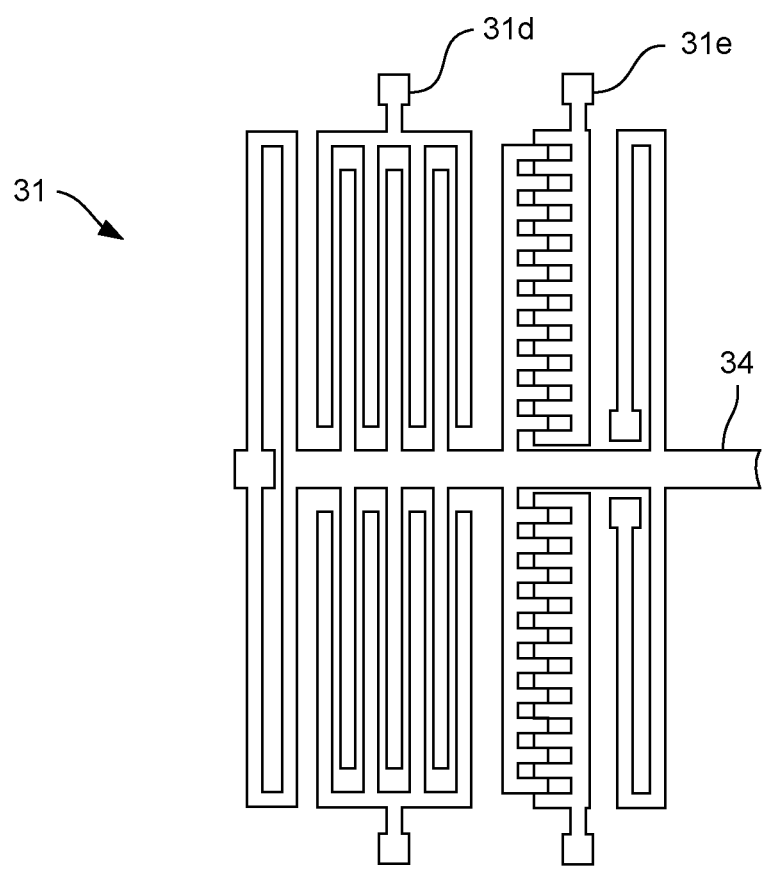

FIG. 9E shows a sensor element 31 including a displacement sensing element 31d and an actuation element 31e.

It should be understood that the present invention is not limited to any particular combination of the sensor elements. Although not illustrated in the drawings, the sensor elements may also be designed to be thermally actuated or piezoelectrically actuated. The sensing element may also be in the form of a piezo resistive sensor.

Although the sensor elements 31 and 32 may have various configurations, they can be manufactured from a silicon substrate in the same way by a known method, e.g., photolithography, using different mask patterns.

Figure 10:
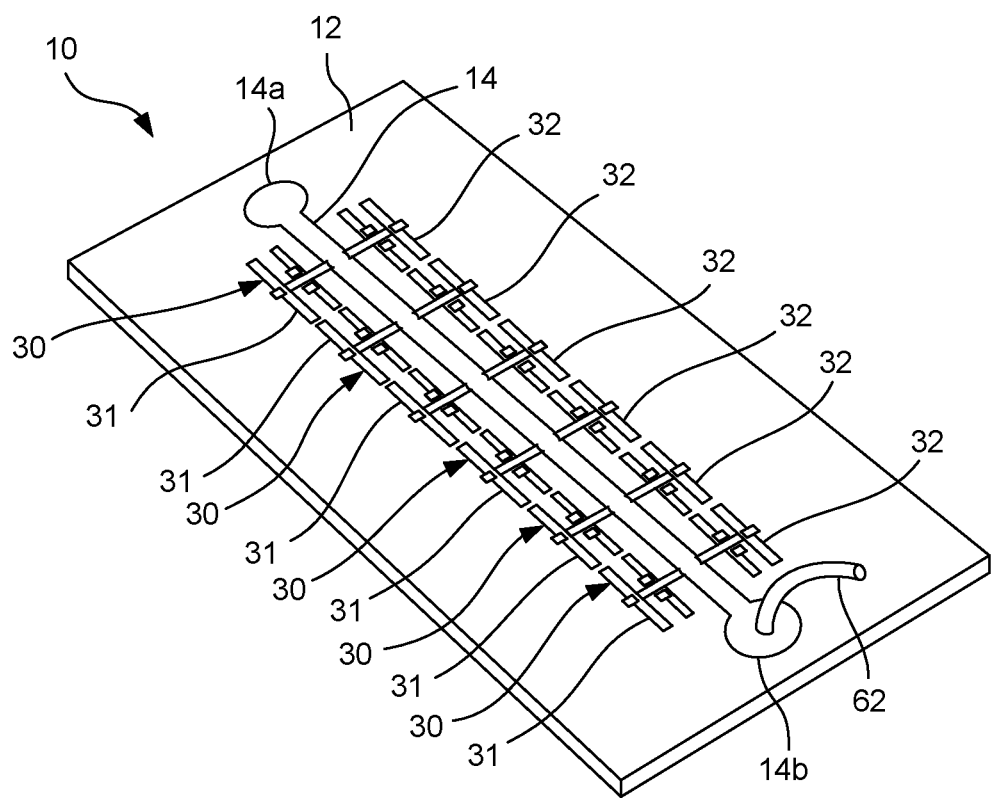
FIG. 10 is a schematic diagram showing a measuring system according to another embodiment.

FIG. 10 shows a measuring system 10 according to another embodiment. The measuring system 10 also has a microfluidic chip 12 formed with a microfluidic channel 14 and a plurality of sensors 30 integrated with the microfluidic chip 12. In contrast to the measuring system 10 shown in FIG. 2, the measuring system 10 according to this embodiment is not provided with the branch channels 18 and the valves 42. Thus, the measuring system 10 does not have a function of sorting cells, depending on the biophysical characteristics of the cells.

This type of the measuring system 10 is used to perform chemical or biological manipulation of the cells by exposing the cell to solution including biochemical reactant. In this case, the solution is supplied from the inlet 14a through the microfluidic channel 14 to make certain that the cells of interest can be characterized under influence of the reactant. For example, the evolution of cells exposed to the reagent may be observed. In order to characterize the cells, the sensor elements 31 and 32 capture a single cell between the tips of arms in the same way as described above with reference to FIG. 6. The reaction of the cell can be obtained through direct manipulation of the cell as the biophysical characteristics of the cells change correspondingly.

Although six sensors 30 are illustrated in FIG. 10 by way of example, the measuring system 10 may include any number of sensors 30 as required.

According to the embodiment in which the measuring system 10 has a plurality of sensors 30 along the microfluidic channel 14, characterization can be performed for more than one cell simultaneously. When the characterization is completed, the cells are all moved to the outlet 14b where they are sucked out of the microfluidic channel 14 by the suction unit 62. Nonetheless, according to an embodiment, the measuring system 10 may also be provided with only one sensor 30.

Figure 11:
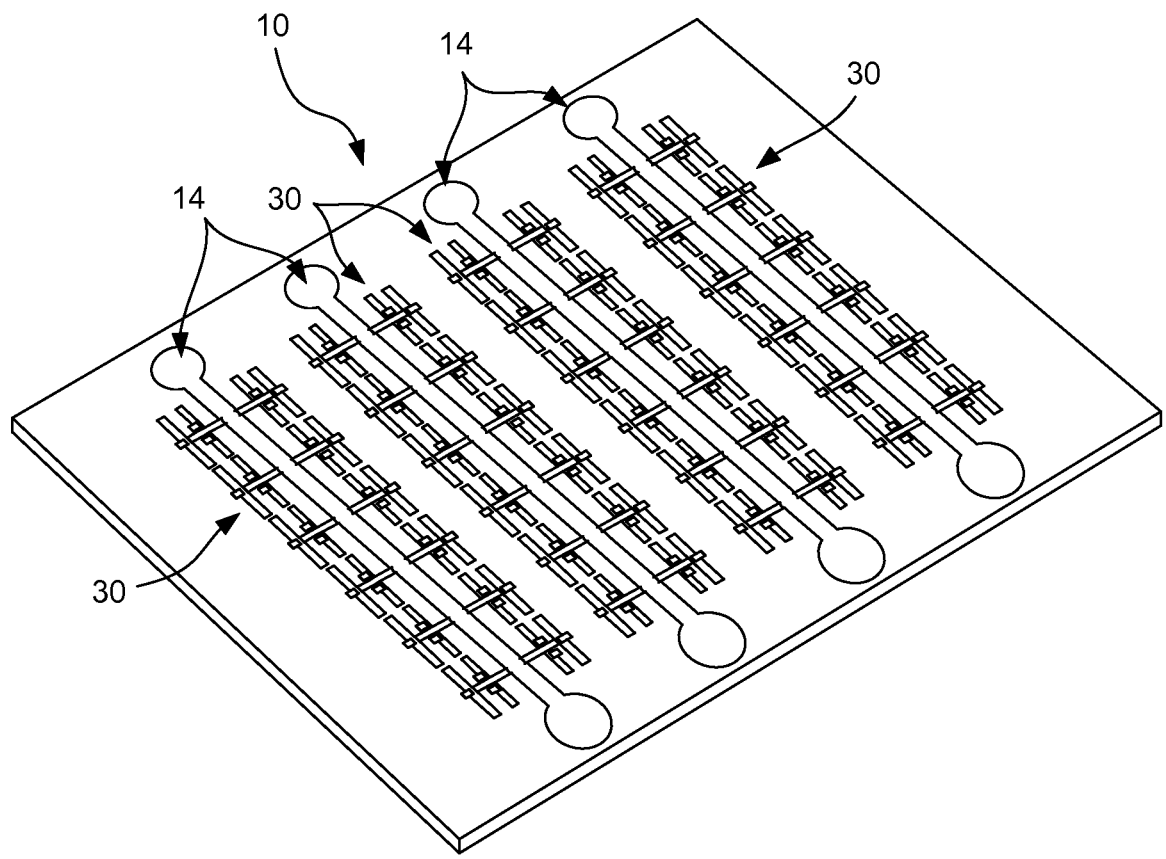
FIG. 11 is a schematic diagram sowing a measuring system according to yet another embodiment.

FIG. 11 shows a measuring system 10 similar to that shown in FIG. 10, but having an increased throughput. Referring to FIG. 11, four separate microfluidic channels 14 are provided in parallel with each other, by way of example. The microfluidic channels 14 can be used independently of each other, and therefore the throughput of the measuring system 10 can be increased as four times. The modular configuration of the measuring system 10 makes it easy to increase the throughput as necessary in combination with one measuring system with another.

In addition, the above-described measuring systems 10 may be configured as a modular device, such that the measuring systems 10 are compatible with other existing apparatus.

Figure 12:
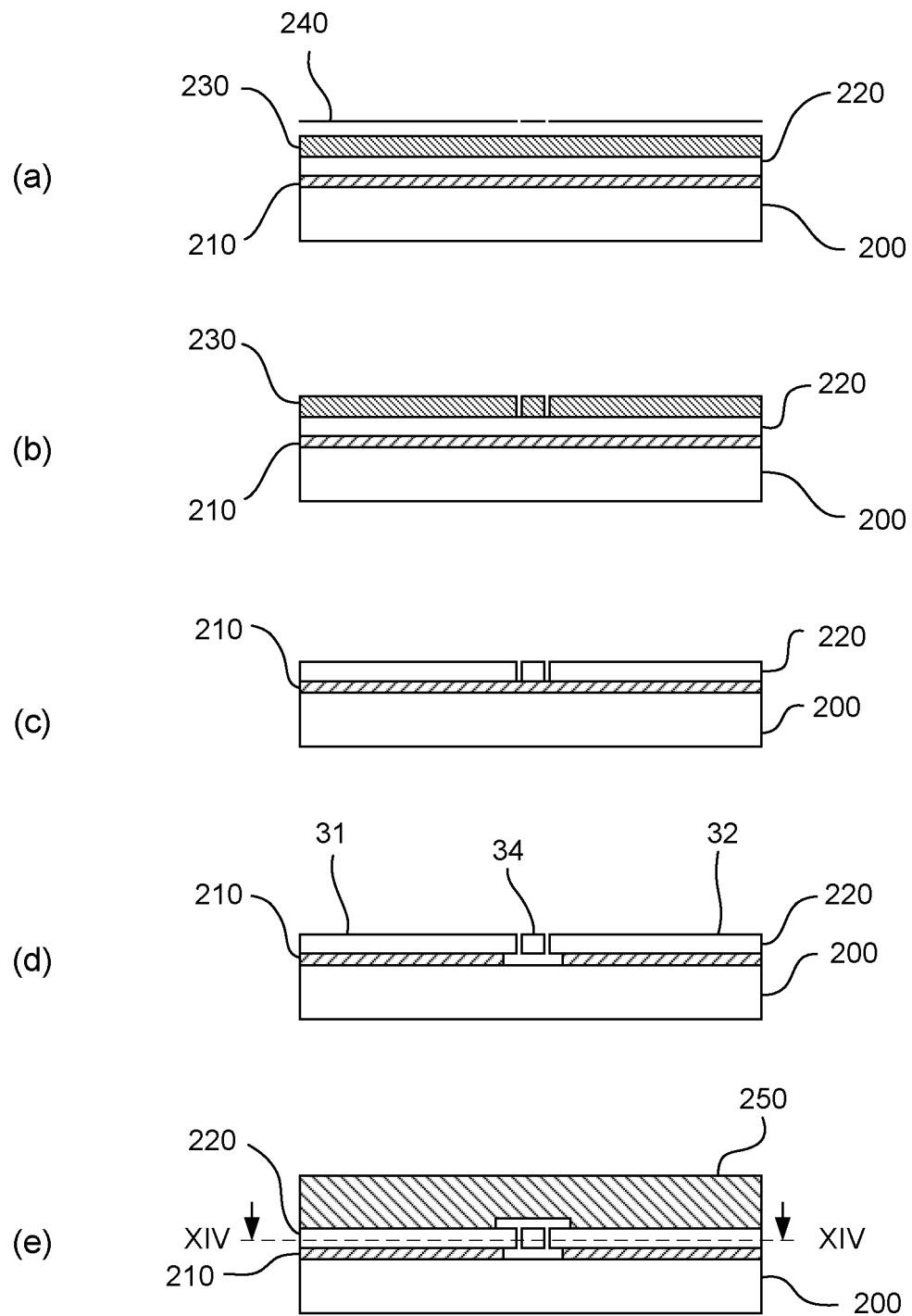
FIG. 12 illustrates a process of manufacturing a sensor element of a measuring system according to an embodiment.
Figure 13:
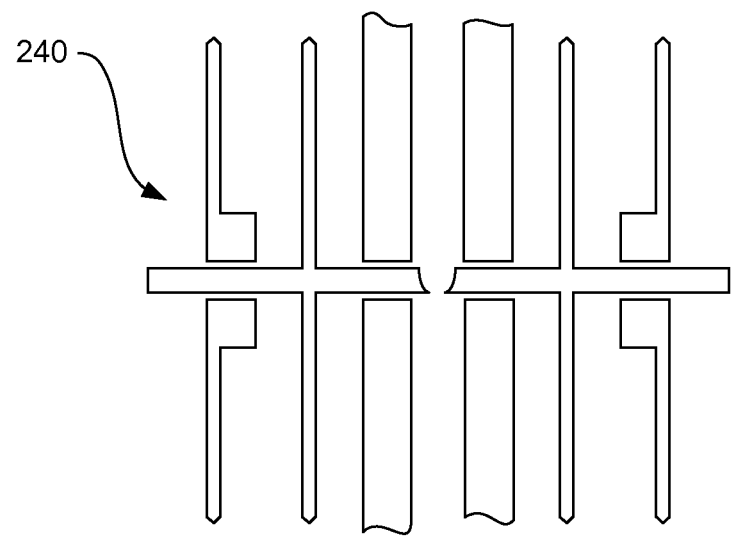
FIG. 13 shows a mask pattern which can be used to manufacture the sensor element in accordance with the process illustrated in FIG. 12.
Figure 14:
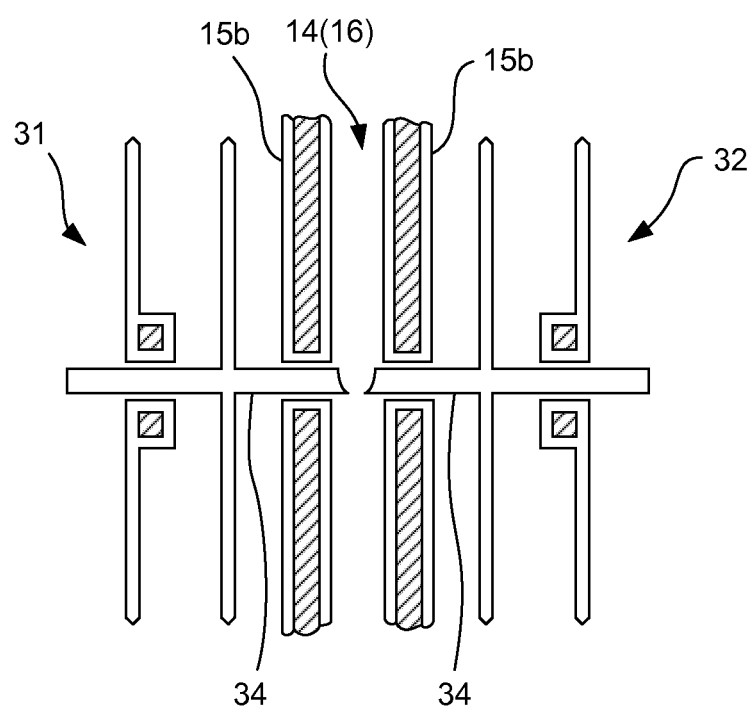
FIG. 14 shows the sensor element produced in accordance with the process illustrated in FIG. 12 by using the mask pattern shown in FIG. 13.

Referring to FIGS. 12 to 14, an exemplary manufacturing process to produce a sensor 30 according to an embodiment will be described.

FIG. 12 illustrates a process of manufacturing sensor elements 31 and 32 of a measuring system 10 according to an embodiment. FIG. 13 shows a mask pattern which can be used to manufacture the sensor elements 31 and 32. FIG. 14 shows the sensor elements 31 and 32 produced by using a mask 240 shown in FIG. 13.

As shown in FIG. 12(a), a multi-layer object and a mask 240 are provided to produce the sensor elements 31 and 32. A bulk silicon layer 200 is disposed at the bottom of the object. An oxide layer 210 is disposed on the top of the bulk silicon layer 200. On the other side of the oxide layer 210, a top silicon layer 220 is provided. Resist 230 forms a top layer of the object.

In order to obtain a desired shape of the sensor elements 31 and 32, the mask 240 is provided. As can be seen in comparison between FIGS. 13 and 14, the mask 240 has a shape corresponding to the sensor elements 31 and 32 and the microfluidic channel 14.

Then, the resist 230 is subjected to insolation through the mask 240 to remove part of the resist 230 according to the mask pattern, as illustrated in FIG. 12(b). Next, the top silicon layer 220 is etched and the resist 230 is removed (FIG. 12(c)).

The oxide layer 210 is then etched to shape the top silicone layer 220 (FIG. 12(d)). At this stage, the arm 34 of the sensor 30 is shaped as well as the sensor elements 31 and 32. Finally, a cap 250 made of PDMS is provided on the top of the top silicon layer 220, to obtain the sensor elements 31 and 32 as well as the microfluidic channel 14 (FIGS. 12 (e) and 14). Referring to FIG. 14, hatched portions represent a stationary part fixedly attached to the base plate of the microfluidic chip.

Accordingly, the integrated sensor 30 is patterned on the base plate of the microfluidic chip 12. The shape of the sensor 30 is obtained with micromachining technique that permits to have the fixed part on the base plate and flexible arm 34. As the sensor elements 31 and 32 and the opening 14c are fabricated on the base plate, the flexible arms 34 are self-aligned with the opening 14c to guaranty the impermeability of the opening 14c and the proper operation of the measuring system 10.

According to the manufacturing process described above, the moving elements such as an actuator and/or sensor and the lateral opening 14c of the channel 14 are patterned with the same mask 240, thus these parts are also self-aligned as a result of the process as shown in FIG. 12. On the other hand, the PDMS cap 250 can be relatively loosely positioned relative to the sensor elements 31 and 32.

The above-described measuring systems 10 facilitate cell specific analysis in the field of biomedical sciences. The possible applications include, but are not limited to, basic research, cancer diagnostics, translational research, drug development, molecular studies, practice of medicine, etc.

In clinical oncology, molecular profiling of isolated circulating tumor cells (CTCs) or microdissected cell populations can yield a global map of "omics" information that (in combination with morphological and biophysical analysis) can provide the basis for diagnosis, prognosis, and individually tailored therapy.

Profiled individual cells (single cell research) also provide additional molecular detail of disease mechanisms and new layers of data for identifying and prioritizing drug targets and therapeutic hypothesis.

The invention claimed is:

1. A system adapted to measure multiple biophysical characteristics of cells, the system comprising:
    a microfluidic chip provided with a microfluidic channel which allows cells to flow through, the microfluidic channel having an inlet, an outlet, and a lateral opening situated between the inlet and the outlet; and
    a capacitive sensor integrated in the microfluidic chip, adapted to obtain biophysical characteristics of a single cell in the microfluidic channel by directly manipulating the single cell by sensor elements positioned through the lateral opening of the microfluidic channel,
    wherein the sensor elements include a pair of arms extending toward each other, tips of the pair of arms being arranged in lateral openings formed on opposite sides of the microfluidic channel,
    the capacitive sensor comprising an electrostatic actuator, a stationary part and a movable part driven by the electrostatic actuator to move relative to the stationary part, the stationary part being fixed to the microfluidic chip, the movable part being arranged in the lateral opening of the microfluidic channel, wherein the movable part comprises at least one arm of the pair of arms which is configured to move closer to or away from the other arm,
    wherein the electrostatic actuator is arranged in an air volume opening into the microfluidic channel through the lateral opening, and
    wherein the lateral openings and the tips of the arms are sized to create an interface between fluid and air in the system, so as to allow the tips of the arms to be introduced into the microfluidic channel through the respective opening while preventing a fluid within the microfluidic channel from leaking into the air volume.

2. The system of claim 1, wherein the sensor is a programmable sensor adapted to selectively obtain one or more biophysical characteristics of the single cell.

3. The system of claim 1, wherein the microfluidic chip is further provided with at least one additional microfluidic channel arranged in parallel with the microfluidic channel.

4. The system of claim 1, wherein the sensor is adapted to obtain biophysical characteristics of the single cell by stimulating the single cell in the microfluidic channel mechanically and/or electrically.

5. The system of claim 1, wherein the sensor is adapted to obtain biophysical characteristics including at least one of size, rigidity, shape recovery time, viscosity, and electrical impedance, and/or frequency dependency of the biophysical characteristics.

6. The system of claim 1, further comprising a collecting means in fluid communication with the outlet of the microfluidic channel.

7. The system of claim 1, further comprising a sorting means for sorting the cells flowing in the microfluidic channel, depending on the biophysical characteristics of the cells obtained by the sensor.

8. The system of claim 7, wherein the microfluidic chip is further provided with at least one branch channel branching off from the microfluidic channel and downstream relative to the sensor.

9. The system of claim 8, wherein the sorting means comprises a valve adapted to direct the cell to the branch channel or downstream of the microfluidic channel, depending on the biophysical characteristics of the cell.

10. The system of claim 8, further comprising a dock in fluid communication with the branch channel.

11. The system of claim 7, wherein the sorting means is adapted to sort the cells by comparing the biophysical characteristics of the cell with a threshold.

12. The system of claim 11, wherein the threshold is programmable.

13. A process of manufacturing the system of claim 1, the process comprising:
    applying a mask pattern corresponding to the shape of the microfluidic channel and the shape of the stationary part and the movable part of the sensor; and
    forming the shape of the sensor together with the microfluidic channel.

14. A process of measuring multiple biophysical characteristics of cells, comprising:
    providing a system according to claim 1;
    flowing cells through the microfluidic channel between the inlet and the outlet;
    directly manipulating a single cell by the sensor through the lateral opening of the microfluidic channel so as to obtain biophysical characteristics of said single cell.

15. The process of claim 14, further comprising stimulating the cell chemically and/or biologically in the microfluidic channel.

16. The process of claim 14, further comprising sorting the cells flowing in the microfluidic channel depending on the biophysical characteristics of the cells obtained by the sensor-.

17. The process of claim 14, wherein the biophysical characteristics include at least one of size, rigidity, shape recovery time, viscosity, and electrical impedance, and/or frequency dependency of the biophysical characteristics.

* * * * *